(12) United States Patent
Kunz et al.

(10) Patent No.: US 9,164,072 B2
(45) Date of Patent: Oct. 20, 2015

(54) SENSOR ELEMENT AND METHOD FOR DETECTING A GAS

(71) Applicant: Robert Bosch GmbH, Stuttgart (DE)

(72) Inventors: Denis Kunz, Untergruppenbach (DE); Wolfgang Menesklou, Ruelzheim (DE); Martin Schreivogel, Bad Berka (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 14/226,905

(22) Filed: Mar. 27, 2014

(65) Prior Publication Data
US 2014/0290339 A1 Oct. 2, 2014

(30) Foreign Application Priority Data
Mar. 28, 2013 (DE) .......................... 10 2013 205 540

(51) Int. Cl.
*G01N 33/00* (2006.01)
*G01N 27/22* (2006.01)

(52) U.S. Cl.
CPC .......... *G01N 33/0027* (2013.01); *G01N 27/227* (2013.01)

(58) Field of Classification Search
CPC ........................ G01N 33/0027; G01N 33/0032
See application file for complete search history.

(56) References Cited

FOREIGN PATENT DOCUMENTS
DE   10 2009 029 621 A1   3/2011

OTHER PUBLICATIONS

Zhu et al.; Amorphous ferroelectric (Ba0.67Sr0.33) Ti1.0203 thin films with enhanced H2 induced interfacial polarization potential; Journal of Applied Physics; Nov. 1, 1998; pp. 5134-5139; vol. 84, No. 9; 1998 American Institute of Physics.

*Primary Examiner* — Laura Martin
*Assistant Examiner* — Alex Devito
(74) *Attorney, Agent, or Firm* — Maginot, Moore & Beck LLP

(57) ABSTRACT

A sensor element for the qualitative and/or quantitative detection of a gas includes a front electrode configured to be exposed to the gas to be measured, a back electrode, and an electrically insulating layer positioned between front electrode and back electrode. The front electrode and the back electrode can be electrically contact connected to an AC voltage source for a qualitative and/or quantitative detection of a gas. The electrically insulating layer is at least locally polarizable in such a way that in a polarized state the electrically insulating layer has a relative permittivity which is lower than in a non-polarized state by a factor in a range of greater than or equal to 1.1.

10 Claims, 4 Drawing Sheets

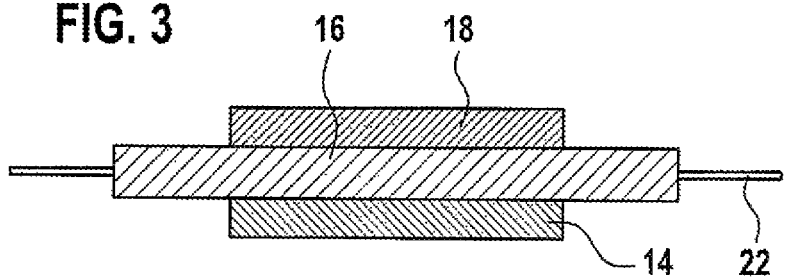
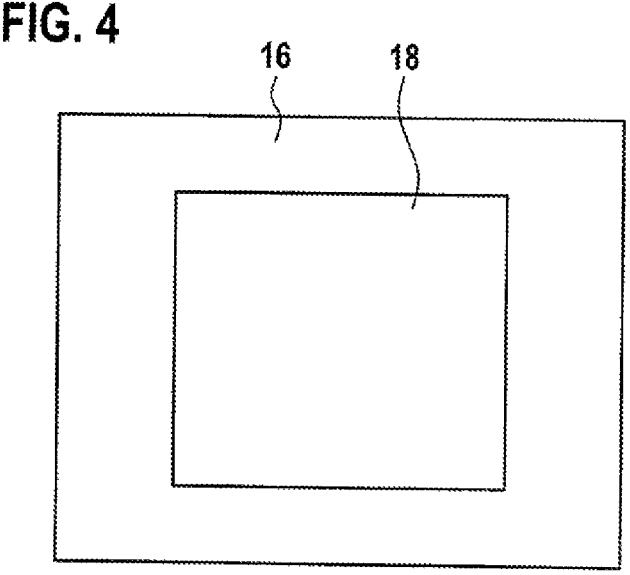

FIG. 5
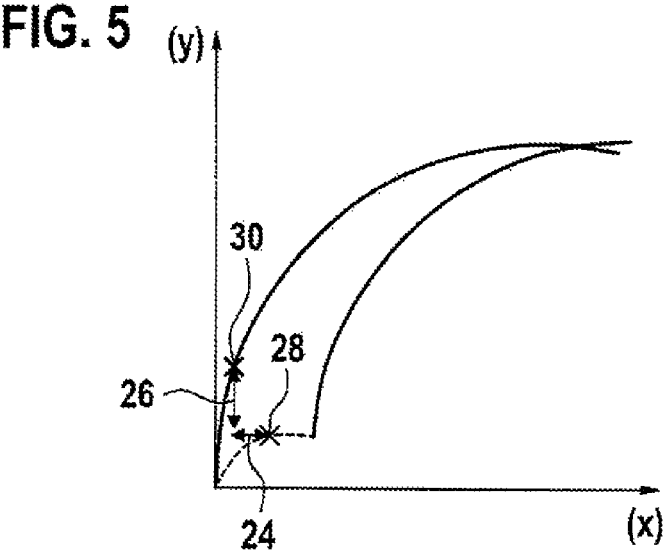
FIG. 6
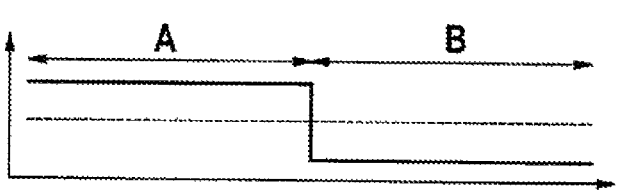
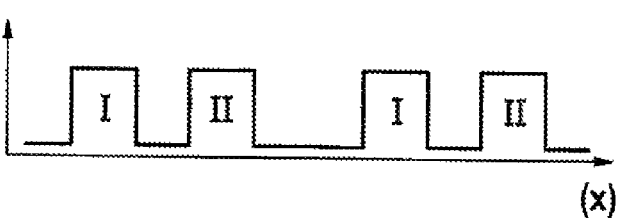

SENSOR ELEMENT AND METHOD FOR DETECTING A GAS

This application claims priority under 35 U.S.C. §119 to patent application no. DE 10 2013 205 540.4, filed on Mar. 28, 2013 in Germany, the disclosure of which is incorporated herein by reference in its entirety.

The present disclosure relates to a sensor element, such as, in particular, a sensor element for the qualitative and quantitative detection of a gas. The present disclosure furthermore relates to a method for detecting a gas.

BACKGROUND

Field effect transistors (FETs) having a gas-sensitive gate have long been researched and used as gas sensors, for instance. Field effect based semiconductor components afford the advantage of very small dimensions, low unit costs and high integrability. For applications at high temperatures, for example, the use of silicon carbide or other semiconductors having a high band gap is known, in order to avoid the intrinsic conduction dominant starting from approximately 250° C. in the case of silicon.

The document DE 10 2009 029 621 A1 discloses a detection device and a method for detecting a gas. In particular, said document describes metal-insulator-semiconductor structures (MIS structures) that are used for detecting gases. In that case, a capacitance structure is used which can consist of at least one gas-sensitive electrode, at least one dielectric, a semiconducting material and a conductive back electrode.

The article W. Zhu et al. Amorphous ferroelectric $(Ba_{0.67}Sr_{0.33})Ti_{0.02}O_3$ thin films with enhanced $H_2$ induced interfacial polarization potential, Journal of Applied Physics, 84(9), pages 5134-5139, 1998, furthermore discloses using specific dielectric layers without a semiconductor substrate in a sensor element, and using DC leakage current as a measurement signal.

SUMMARY

The present disclosure relates to a sensor element for the qualitative and/or quantitative detection of a gas, comprising a front electrode, which can be exposed to the gas to be measured, a back electrode and an electrically insulating layer arranged between front electrode and back electrode, wherein the front electrode and the back electrode can be electrically contact-connected to an AC voltage source for a qualitative and/or quantitative detection of a gas, and wherein the dielectric layer is at least locally polarizable in such a way that in the polarized state it has a relative permittivity which is lower than in a non-polarized state by a factor in a range of greater than or equal to 1.1, in particular 1.5.

A sensor element described above can advantageously allow the qualitative and/or quantitative detection of gases in a highly sensitive and highly selective manner in a wide temperature range.

For this purpose, the sensor element comprises a front electrode, which can be exposed to the gas to be measured, a back electrode and an electrically non-conductive or electrically insulating layer arranged between front electrode and back electrode. In this case, said layer can have, in particular, a conductivity or an electrical resistance such as is known in principle for such sensor elements. Exemplary values lie in a range of $10^{-8}$ S/m, wherein conductivities of up to $10^{-3}$ S/m or, depending on the specific application, even higher can also be possible.

In this case, the front electrode is, in particular, the electrode which can be exposed to the gas to be measured, or faces the gas to be measured. In particular, the front electrode comes directly into contact with the gas to be measured. In this case, the front electrode can be fashioned, in particular, from a metal or else from an organic electrically conductive material, such as from the class of phthalocyanines, for example. This can make possible, in particular, a particularly good stability of the front electrode or of the sensor arrangement. By way of example, the electrode can comprise one or more catalytically active materials in order to enable a selectivity with regard to different gases. The catalytically active materials can comprise, for example, platinum (Pt), palladium (Pd), gold (Au), rhodium (Rh), rhenium (Re), ruthenium (Ru), iridium (Ir), titanium (Ti), titanium nitride (TiN), tantalum nitride (TaN) or alloys comprising one or more of the abovementioned components. In this case, the front electrode can be produced completely from one or more of the abovementioned substances, or comprise such materials only in part, for instance in the form of particles arranged in an electrode structure.

In this case, the front electrode can be designed, in particular, in the case of an interaction with a substance to be measured, such as a gas to be measured, for instance, to set a variable electrical characteristic of the sensor element to an electrical characteristically that can be assigned to the gas. In this case, in the context of the disclosure, substances to be measured other than gaseous substances to be measured are also equally encompassed hereinafter, without reference being made thereto explicitly whenever exemplary gaseous substances are discussed. In this case, the variable electrical characteristic can comprise for example a real or imaginary part of the impedance, a capacitance value, a conductance or a resistance value of the sensor element. In this case, the electrical characteristic can be varied if the interaction takes place between the gas to be measured and the front electrode. In this case, the interaction can presuppose a direct contact between the gas, for example, and the front electrode. The interaction can comprise for example a disassociation of the gas at the surface of the front electrode or a diffusion of the gas into the front electrode. Depending on the interacting gas to be measured, the variable electrical characteristic can be set to a specific value. In this case, the specific value can be dependent on the type and also on the concentration of the gas, such that both a qualitative and a quantitative measurement are possible. In order to detect the specific value of the variable electrical characteristic, contacts of the front electrode and of the back electrode can be contact-connected to a corresponding measuring device. By way of example, the impedance, the capacitance value, conductance or the resistance value of the sensor element can be detected by means of the measuring device. By means of a further evaluation unit, the gas and/or its concentration can be deduced from the detected electrical characteristic of the sensor element. This can be realizable for example on the basis of a look-up table comprising an assignment between the gas to be detected and the electrical characteristic of the sensor element. Such characteristics, in particular, can be metrologically detected and evaluated in a simple manner. By way of example, the complex impedance can be detected by means of an AC voltage measurement.

In principle, the back electrode can be fashioned from the same material as described above for the front electrode. In the case of the configuration composed of a metal, it is possible to increase the robustness of the sensor arrangement relative to degradation. Furthermore, the back electrode can be fashioned for example from a semiconductor material, such as, for example, silicon (Si), germanium (Ge), gallium arsenide (GaAs), indium-phosphorus (InP), silicon carbide (SiC), gallium nitride (GaN), or other semiconductors. One feature for the semiconductor material chosen can advantageously be that it has an electrical conductivity within the entire operating temperature range. This can be achieved in particular by virtue of the lower limit of the operating temperature range of the sensor arrangement being arranged above a temperature at which the intrinsic conduction of the semiconductor material commences. Furthermore, the semiconductor material can be chosen such that no depletion occurs at least in the operating range of the sensor arrangement. In this case, the electrical conductivity can either be an intrinsic electrical conductivity, or one based on dopings.

Furthermore, the back electrode can be applied on a substrate, for example. In this case, the substrate can be fashioned from an electrically insulating material, such as sapphire, for instance.

The dielectric or electrically insulating layer arranged between front electrode and back electrode can furthermore be fashioned for example from a known electrically insulating material.

Non-restrictive examples which can be used as a dielectric include for example oxides, such as, for instance, aluminum oxide ($Al_2O_3$) and silicon dioxide ($SiO_2$), or nitrides, such as, for example, silicon nitride ($Si_3N_4$), or the like.

Consequently, the front electrode, the back electrode and the electrically non-conductive or dielectric layer form a capacitance structure that can serve as a basis for the sensor according to the disclosure.

Furthermore, the electrically insulating layer is at least locally polarizable. In the sense of the present disclosure that can mean, in particular, that the entire electrically insulating layer is polarizable, or that the layer is also polarizable only in a locally delimited manner and can have dipoles that are oriented or can be aligned approximately parallel, or that a certain amount of polarity can be producible at least in a spatially delimited manner in the layer. In this case, a polarizability can be understood to mean, in principle, the alignment of electrical charges or dipoles for a polarizability at atomic or molecular level, which can extend over a large, macroscopic region, or furthermore the displacement of electrical charges through a region for generating a polarizability of said region or a space charge polarization. In this case, the polarity can be altered in terms of its alignment in particular by means of the application of a voltage, such as an AC voltage, for instance, to the front electrode and the back electrode. For this purpose, the front electrode and the back electrode can have corresponding contacts, for example. Consequently, the front electrode and the back electrode can serve, inter alia, for impressing an electric field into the dielectric layer or for influencing the gas reaction.

In this case, the dielectric layer has in the polarized state an electric field-dependent relative permittivity which is lower than in a non-polarized state by a factor in a range of greater than or equal to 1.1, in particular in the entire layer or only in the polarizable region. In the sense of the disclosure that can mean, in particular, that in a fully polarized state, for instance as a result of the application of a bias voltage, if the charges or dipoles are virtually fully aligned by the voltage, the permittivity is lower by the abovementioned factor than in a non-aligned state of the dipoles or with polarity not generated, for instance as a result of the absence of a bias voltage or of an electric field, or, in particular, in the state in which the dipoles or charges, for example, can be aligned the most easily, that is to say that a preferred direction is not predefined by an impressed electric field. Particularly in the case of a combination of the above-mentioned arrangement, particularly in conjunction with an AC voltage having a frequency which is configured as AC voltage frequency a resonant frequency for an alternating alignability corresponding to the polarization frequency of the polarizable material, the measurement behavior of a sensor arrangement described above can be influenced particularly positively. In detail, a selectivity with regard to different gases can be produced as a result of the targeted introduction of polarizable species solely as a result of the application of different bias voltages. Depending on the strength of the present polarization mechanism, very strong signal changes in relation to an inert gas are possible in this case.

A wide variety of evaluation methods are conceivable in this case. In particular, the current-voltage measurement and impedance measurement are methods that can be implemented electronically in a simple manner, such that simple evaluation circuits known to the person skilled in the art in principle from the field of MEMS acceleration sensors, for example, can suffice. Furthermore, since no semiconductor is required as substrate, effects associated therewith, such as, for instance, the charge reversal of interfacial states which can lead to a signal drift, have no influence. Consequently, the abovementioned sensor structures, in particular in delimitation with respect to FETs or MIS structures, react particularly insensitively toward threshold voltage changes with regard to trapped charges in the gate dielectric or at the interface with the semiconductor, which could lead to a considerable drift of the signal in long-term operation, with the result that, according to the disclosure, corrections of the measurement signal in particular for short measurement times, or measurement times that are not too long, are not required or are required only in a reduced manner.

As a result of the configuration of the above-described sensor with the evaluation methods thereby possible in particular using an AC voltage, a particularly selective and sensitive measurement behavior can be realizable. In this case, the above-described measurement behavior can be realizable, in particular, by means of a particularly wide temperature range, namely for example from room temperature through to 1000° C. or even higher.

Furthermore, the structures described in the case of such a sensor element can be produced or processed particularly simply and with known and readily controllable and adaptable method steps. In other words, it becomes possible that as a result of the small number of required process steps for the production of a sensor arrangement described above, the proposed gas sensors can be produced significantly more cost-effectively than comparable FET or MIS structures.

Furthermore, many of such measuring structures can be integrated or combined on just one chip. As a result, the diversity of use of such a sensor arrangement can be greatly increased since a multiplicity of differently configured sensor arrangements can be arranged in an extremely small space, which can enable a wide variety of measurements by means of just one measuring arrangement. By way of example, selectivities for a multiplicity of different gases to be measured can be made possible by the combination of different, correspondingly designed gas-sensitive electrodes.

In the context of one configuration, the at least local polarizability of the electrically insulating layer can be producible by the provision of mobile ions, defect associations, polar atomic groups or polar domains in the dielectric layer.

With regard to the mobile ions, these can be for example sodium ions ($Na^+$), potassium ions ($K^+$), calcium ions ($Ca^{2+}$), or the like, which can lead to a space charge polarization when an electric field is applied. The ions can be introduced during or after layer deposition, for example using an ion gun or ion source such as is known to the person skilled in the art for instance for the doping of semiconductors, or else by the application of an ion-containing solution and a suitable heat treatment step, such that the ions can diffuse into the layer. Through a suitable choice of the material of the electrically insulating layer, such as, for instance, $SiO_2$, $Al_2O_3$, $Si_3N_4$, the diffusion constant of the ions and thus the resonant frequency of the polarization, which advantageously corresponds to the frequency of an AC voltage introduced, can be set. In this configuration, the operating temperature of the sensor arrangement can lie for example in a range of greater than or equal to 200° C., in order to ensure a particularly advantageous and thus effective mobility of the ions. In particular the sensitivity of the sensor arrangement can be increased as a result.

With regard to the polar materials or polar atomic groups, in particular ferroelectrics can be mentioned here. Polar materials can thus be, in particular, such materials whose elementary cells, on account of their lattice structure, have an electric dipole moment that can be aligned in the electric field. Non-restrictive examples include, for instance, barium titanate ($BaTiO_3$), lead zirconate titanate $Pb(Zr_xTi_{1-x})O_3$, wherein X lies in a range of greater than or equal to 0 to less than or equal to 1, or barium strontium titanate $Ba_xSr_{1-x}TiO_3$, wherein X preferably lies in a range of greater than or equal to 0 to less than or equal to 1. Materials having a low coercive field strength should preferably be used, in order to enable rapid polarity reversal or alternating alignment or arrangement of charges in the alternating electric field.

Ferroelectrics can be used for this application in particular below the ferroelectric Curie point; for thin-film layers, however, the phase transition extends over a wide temperature range, such that ferroelectric properties are still observed even at relatively high temperatures; by way of example, the Curie point is up to 500° C. depending on the composition in the case of lead zirconate titanate (PZT).

With regard to polarizable defect associations, these can be formed, in particular, by impurity atoms which, as a result of defects, can enable a voltage-based, such as in particular AC voltage-based, charge transfer and thus a change in the alignment of a dipole, this effect understandably occurring to an increased extent in a microstructure in order to amplify the effect. A non-restrictive example can be seen in monovalent impurity atoms which are bonded to an amorphous $SiO_2$ microstructure, for example, via non-bridge-forming oxygen ions.

Spatially polar regions or domains can be, in particular, such regions within which, for example, mobile ions can migrate through the layer and can correspondingly become arranged at the boundary of the corresponding region or of the corresponding domain. In this case, with a bias voltage, for example, the regions can be locally delimited within the layer or have an extent over the entire layer. Consequently, spatially polarizable regions are configured in such a way that they constitute a regional boundary for the polarizability, that is to say for instance for the movement of mobile ions, such as, for instance, a grain having a specific morphology. By way of example, the polarizable regions can be arranged in a "sandwich structure". In detail, in this configuration, regions of low polarizability could be arranged near the contacts for the purpose of better insulation, and a layer or a region having high polarizability and furthermore comparatively high conductivity could be arranged between these regions.

In the context of a further configuration, the electrically insulating layer can comprise an electrically insulating material selected from the group consisting of oxides, such as, in particular, silicon dioxide ($SiO_2$), aluminum dioxide ($Al_2O_3$), hafnium oxide ($HfO_2$), tantalum oxide ($Ta_2O_5$), zirconium oxide ($ZrO_2$), nitrides, such as, in particular, silicon nitride ($Si_3N_4$), boron nitride (BN), carbides, such as, in particular, silicon carbide (SiC), and silicides, such as, in particular, tungsten silicide ($WSi_2$), tantalum silicide ($TaSi_2$), and ferroelectric materials, such as, for example, barium titanate ($BaTiO_3$), lead zirconate titanate $Pb(Zr_xTi_{1-x})O_3$ or barium strontium titanate $Ba_xSr_{1-x}TiO_3$. In this configuration, in particular, an effective electrically insulating or dielectric layer can be formed which is furthermore suitable for being polarizable at least in a locally delimited manner. In detail, the abovementioned substances are sufficiently inert, such that polarizable species can be introduced into them and furthermore can also be present alongside one another under the operating conditions of a sensor without significant interactions.

In the context of a further configuration, at least one of the front electrode, the back electrode and the electrically insulating layer, in particular the electrically insulating layer, can have a thickness which is in a range of less than or equal to 10 µm, for example less than or equal to 200 nm. Such structures can be producible for example by thin-film methods known per se. By way of example and without restriction mention shall be made here of CVD (Chemical Vapor Deposition) methods, such as, for instance, LPCVD (Low Pressure CVD) or PECVD (Plasma Enhanced CVD), ALD (Atomic Layer Deposition) methods, PLD (Physical Layer Deposition) methods, thermal oxidation, plasma methods or sputtering or vapor deposition methods. This enables a very compact construction in conjunction with, moreover, low production costs and also the integrability into conventional production processes from microsystems engineering.

In the context of a further configuration, the front electrode can be porous and/or fashioned from particles. By way of example, in this configuration, pores in the nanometers range can be present by virtue of the particles for example having a size in the range of 5 nm or more, such that the electrode is configured as porous in a nanostructured fashion. In this configuration, the gas to be measured can diffuse or drift into the electrode, such that an interaction of the gas to be measured in accordance with a gas adsorption/work function change at that side of the electrode which faces the dielectric is possible in a particularly advantageous manner.

In the context of a further configuration, the front electrode can be selectively permeable to a gas to be measured. In this configuration, the front electrode can therefore have a surface that is closed, approximately, for other gases. Consequently, an interaction at the interface between electrode and polarizable thin-film layer can take place only with gases which can diffuse or drift through the respective electrode. Diffusion or drifting of other gases into the front electrode through the closed surface can thus be prevented or at least inhibited. A particularly good selectivity and sensitivity can be obtained as a result. This configuration can be realizable, for example, by establishing pores or channels in the electrode by establishing the size of particles from which the electrode is constructed.

In the context of a further configuration, the back electrode can be exposable to a gas to be measured. In this configuration, the back electrode, like the front electrode as well, can thus be embodied in an exposed fashion, in particular, and therefore cannot or at least cannot completely be applied on a substrate. Alternatively, a substrate can be configured with a sufficient porosity and thus gas permeability to the back electrode. In this configuration, the sensor element can be arranged, in particular, between a first gas space and a second gas space with a reference gas, such that the interaction of the front electrode with the gas or a first gas to be measured and a further interaction of the back electrode with the reference gas as second gas to be measured can be carried out. Consequently, by means of the first interaction of the front electrode and by means of the further interaction of the back electrode, a variable electrical characteristic of the sensor element can be set to the electrical characteristic that can be assigned to the guest. The reference gas used can be, for example, an inert gas, ambient air or around a defined gas concentration, such as, for instance, pollutant gas concentration. In this case, the electrical characteristic of the back electrode can be the same as that described above for the front electrode. Furthermore, in this configuration, the back electrode, like the front electrode as well, can be impermeable or else porous to a gas to be measured.

With regard to further advantages and features of the sensor element described above, reference is hereby explicitly made to the explanations in connection with the sensor arrangement according to the disclosure and the method according to the disclosure. Moreover, features according to the disclosure and advantages of the sensor element according to the disclosure are intended also to be applicable to and to be deemed to be disclosed for the method according to the disclosure and the sensor arrangement according to the disclosure, and vice versa. The disclosure also encompasses all combinations of at least two features disclosed in the description and/or the claims.

The present disclosure furthermore relates to a sensor arrangement, comprising at least one sensor element configured as described above and a voltage source for applying a voltage to the front electrode and the back electrode, wherein the electrically insulating layer is at least locally polarizable by the voltage that can be applied, and wherein provision is furthermore made of an evaluation unit for the qualitative and/or quantitative assignment of at least one electrical characteristic of the sensor element on the basis of a measurement signal obtained via contacts of the front electrode and of the back electrode on the basis of the polarizability.

A sensor arrangement mentioned above can advantageously allow the qualitative and/or quantitative detection of gases in a highly sensitive and highly selective manner in a wide temperature window.

In particular as a result of the provision of an above-described sensor element comprising a front electrode, a back electrode and a dielectric or electrically insulating layer arranged between front electrode and back electrode, wherein the electrically insulating layer is at least locally polarizable in such a way that in the polarized state it has a relative permittivity which is lower than in a non-polarized state by a factor in a range of greater than or equal to 1.1, in combination with the provision of a voltage source, wherein the electrically insulating layer is at least locally polarizable by the voltage that can be applied, the measurement behavior of a sensor arrangement described above can be influenced particularly positively. In detail, as a result of the targeted introduction of polarizable species and as a result of the application of an AC voltage and/or of a DC voltage by an AC voltage source and/or a voltage source, as explained above, an extremely accurate and extremely selective detection can be made possible. This is because a selectivity with regard to different gases can be produced for example as a result of the application of different DC voltages as bias voltages, wherein the selective gases are then detectable very accurately by means of the AC voltage, wherein in particular the polarization frequency of the dielectric layer corresponds to the frequency of an AC voltage that can be generated by the AC voltage source. In this case, very strong signal changes are possible depending on the strength of the present polarization mechanism.

A wide variety of evaluation methods are conceivable in this case. In particular, current-voltage measurements or impedance measurements are a method that can be implemented electronically in a simple manner, such that simple evaluation circuits known to the person skilled in the art in principle from the field of MEMS acceleration sensors, for example, can suffice. Furthermore, since no semiconductor is required as substrate, effects associated therewith, such as, for instance, the charge reversal of interfacial states which can lead to a signal drift, have no influence. Consequently, the abovementioned sensor structures, in particular in delimitation with respect to FETs or MIS structures, react particularly insensitively toward threshold voltage changes with regard to trapped charges in the gate dielectric or at the interface with the semiconductor, which lead to a considerable drift of the signal during long-term operation, which must be corrected in a complex manner.

As a result of the configuration of the sensor arrangement described above and/or of the above-described sensor with the evaluation methods thereby possible in particular using DC voltage and/or AC voltage, a particularly selective and sensitive measurement behavior can be realizable. In this case, the above-described measurement behavior can be realizable, in particular, by means of a particularly wide temperature range, namely for example from room temperature through to 1000° C. or even higher.

With regard to further advantages and features of the sensor arrangement described above, reference is hereby explicitly made to the explanations in connection with the sensor element according to the disclosure and the method according to the disclosure. Moreover, features according to the disclosure and advantages of the sensor arrangement according to the disclosure are intended also to be applicable to and to be deemed to be disclosed for the method according to the disclosure and the sensor element according to the disclosure, and vice versa. The disclosure also encompasses all combinations of at least two features disclosed in the description and/or the claims.

The present disclosure furthermore relates to a method for the qualitative and/or quantitative detection of a gas, comprising the following method steps:
  a) providing a sensor arrangement described above;
  b) applying a voltage to the front electrode and the back electrode;
  c) exposing at least the front electrode to a gas to be measured; and
  d) qualitatively and/or quantitatively assigning at least one electrical characteristic of the sensor element on the basis of a measurement signal obtained via contacts of the front electrode and of the back electrode on the basis of the polarizability of the dielectric layer of the sensor element of the sensor arrangement.

A method described above can advantageously allow the qualitative and/or quantitative detection of gases in a highly sensitive and highly selective manner in a wide temperature window, wherein the abovementioned method steps can be carried out, in principle, in a freely selectable order and at least partly simultaneously.

For this purpose, the method according to method step a) comprises providing a sensor arrangement configured as described above. In detail, in this regard reference is made to the above explanations concerning the sensor arrangement and concerning the sensor element.

In principle, the method described above thus uses, for detecting gases, a capacitance structure whose insulator comprises at least one electrically insulating or dielectric layer. Said layer can be, in particular, a thin-film layer having a thickness of in particular less than 10 μm, preferably less than 200 nm, and can in this case comprise one or a plurality of partial layers. In this case, at least one of the present dielectric or electrically insulating thin-film layers contains at least one polarizable species or is polarizable at least in a locally delimited manner. In this case, the polarizability is effected at a specific excitation energy and resonant frequency, which can be chosen in a manner dependent on the polarizable species. Preferably the resonant frequency lies in a range of between greater than or equal to 0.1 Hz and less than or equal to 10 MHz. These polarizable species can be mobile ions, for example, which lead to a space charge polarization. Furthermore, defect associations, polar atomic groups or spatially extensive polar regions (domains) are appropriate, for example.

Method step b) involves applying a voltage, such as an AC voltage and/or a DC voltage, to the front electrode and the back electrode, and method step c) involves exposing at least the front electrode to a gas to be measured. In this case, for example, in method step b), before or during the process of applying an AC voltage to the front electrode and the back electrode, a bias voltage, in particular a DC voltage, can be applied.

In other words, by way of example and without restriction, in an evaluation method for generating a sensor signal that is selective with regard to oxidizing and reducing gases, or in principle between gases that bring about a positive or negative work function change at the electrode, a bias voltage can be applied to the sensor element, which bias voltage fixes the polarizable species in a specific polarization state. An interaction of the gas species to be measured with the electrode is then made possible. Adsorbed gas species, for example, can compensate for said bias voltage by a work function change at the electrode. In this regard, by means of a positive bias voltage, it is possible to achieve selectivity for gases which bring about a negative work function change, and vice versa. This then leads to mobile or polarizable species which can lead to an additional contribution in the impedance response of the component as measurement signal. The measurement signal can be picked up by contacts at front electrode and back electrode, and an electrical characteristic of the sensor element can be determined on the basis of the measurement signal.

In this case, a measurement signal can likewise be obtained without the application of a bias voltage, but the selectivity can be increased even further by means of a bias voltage.

Consequently, qualitatively and/or quantitatively assigning at least one electrical characteristic of the sensor element on the basis of a measurement signal obtained via contacts of the front electrode and of the back electrode in accordance with method step d) can be effected on the basis of the polarizability of the dielectric layer of the sensor element.

In this case, by way of example and without restriction, the sensor signal can be evaluated with the aid of impedance measurements. In the latter, it is possible to map, for instance, the effect of different polarization mechanisms in the form of a change in the real or imaginary part. In this case, the measurement frequency of the AC voltage is preferably in the range of the resonant frequency of the relevant mechanism or lower.

In this case, a measurement described above is effected, in particular, within an operating temperature range of the sensor arrangement. This can lie in particular in a range of greater than or equal to room temperature, such as 22° C., in particular, through to 1000° C.

With regard to further advantages and features of the method described above, reference is hereby explicitly made to the explanations in connection with the sensor element according to the disclosure and the sensor arrangement according to the disclosure. Moreover, features according to the disclosure and advantages of the method according to the disclosure are intended also to be applicable to and to be deemed to be disclosed for the sensor arrangement according to the disclosure and the sensor element according to the disclosure, and vice versa. The disclosure also encompasses all combinations of at least two features disclosed in the description and/or the claims.

BRIEF DESCRIPTION OF THE DRAWINGS

Further advantages and advantageous configurations of the subjects according to the disclosure are illustrated by the drawings and explained in the description below. In this case, it should be noted that the drawings are only descriptive in character and are not intended to restrict the disclosure in any form. In the figures:

FIG. 3 shows a schematic illustration of a sectional view through a further configuration of a sensor element;

FIG. 4 shows a schematic illustration of a plan view of the configuration of the sensor element according to FIG. 3;

FIG. 5 shows a schematic illustration of an impedance spectrum in the complex plane, measured using a sensor element according to the disclosure;

FIG. 6 shows a basic schematic diagram for the operation of the sensor arrangement with bias voltage-dependent gas selectivity.

DETAILED DESCRIPTION

Figure 1:
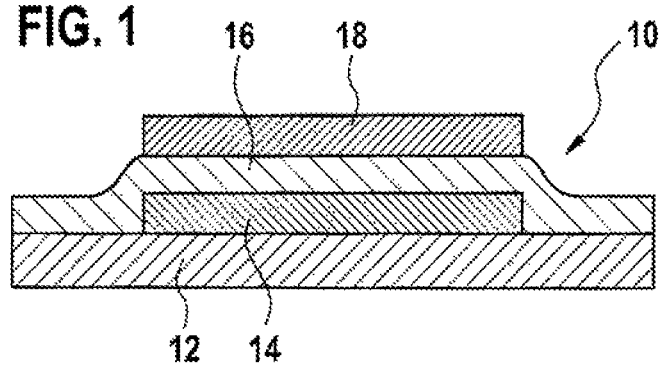
FIG. 1 shows a schematic illustration of a sectional view through a first configuration of a sensor element.

FIG. 1 shows a schematic illustration of a cross section of a first configuration of a sensor element 10 according to the disclosure. In the configuration in accordance with FIG. 1, the sensor element 10 comprises a layer construction having an electrically insulating substrate 12, to which a back electrode 14 is applied, for example by means of sputtering, lift-off or comparable methods. Alternatively, the back electrode 14 can also be defined by local conductivity differences in the substrate material, such as by means of dopings, in particular.

Moreover, a wafer doped overall up to metallic conductivity or a semiconductor having intrinsic conduction at the respective operating temperature can be used as the back electrode 14. Furthermore, at least one electrically insulating dielectric layer 16 is applied on the back electrode 14, for instance by means of sputtering or atomic layer deposition (ALD), and separates the back electrode 14 and a front electrode 18 from one another. In other words, the sensor element 10 is configured as a gas-sensitive capacitance, wherein the front electrode 18 and the back electrode 14 each form a capacitor electrode. The capacitance can be defined in particular by the structure of the front electrode 18.

The front electrode 18 can be fashioned for example from platinum, palladium, gold or aluminum or else from organic materials such as phthalocyanines and can likewise be applied by known deposition methods, the above examples not being restrictive. The front electrode 18, which can also be designated as the gas electrode, can optionally be porous or selectively permeable only to gases to be detected. In the former case, a wide variety of gases can reach the relevant metal-dielectric interface. In the latter case, given a suitable choice of the electrode material or the configuration thereof, for example pore size, for example only hydrogen ions can diffuse to the interface. A selectivity of the sensor element 10 for specific substances such as gases, in particular, can be produced in this way. The front electrode 18 can be deposited by means of chemical or physical methods. Furthermore, the back electrode 14 and the front electrode 18 can be electrically contact-connected to an AC source for a qualitative and/or quantitative detection of a gas.

With regard to the dielectric layer 16, the latter is at least locally polarizable in such a way that it has in the polarized state a relative permittivity which is lower than in a non-polarized state by a factor in a range of greater than or equal to 1.1. By way of example, the locally delimited polarizability of the dielectric layer 16 is producible by the provision of mobile ions, defect associations, polar atomic groups or polar domains. Furthermore, the electrically insulating dielectric layer 16 can comprise an electrically insulating material selected from the group consisting of oxides, such as, in particular, silicon dioxide, aluminum dioxide, hafnium oxide, tantalum oxide, zirconium oxide; nitrides, such as, in particular, silicon nitride, boron nitride; carbides, such as, in particular, silicon carbide; and silicides, such as, in particular, tungsten silicide, tantalum silicide, or ferroelectric materials.

Figure 2:
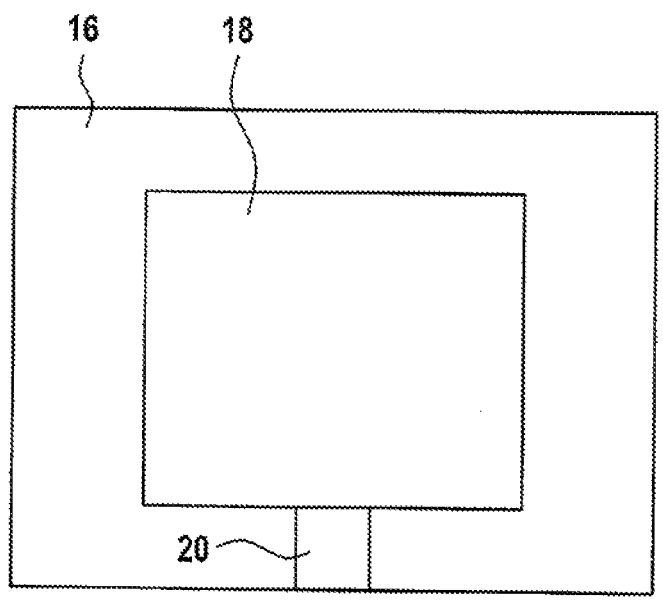
FIG. 2 shows a schematic illustration of a plan view of the configuration of the sensor element according to FIG. 1.

FIG. 2 shows a plan view of the configuration in accordance with FIG. 1, wherein in particular the electrically insulating dielectric layer 16 and the front electrode 18 can be seen. Furthermore, a suitable lead 20 is shown, which can be passivated, if appropriate, for example can likewise be covered by the electrically insulating dielectric layer 16. The lead 20 can serve for making contact with the back electrode 14, for example. A corresponding lead or contact-connection, not shown in FIG. 2, can likewise be provided for the front electrode 18.

FIG. 3 shows a further configuration of a sensor element 10, which configuration largely corresponds to the configuration in FIG. 1, such that corresponding components are provided with the same reference signs and, for the detailed description, reference is made to the description concerning FIG. 1. In the configuration in accordance with FIG. 3, the back electrode 14 can be exposed to a gas to be measured. This can become possible by virtue of the fact that the layer stack can be embodied with one or a plurality of electrically insulating dielectric layers 16 made freely available. An electrode, as described for FIG. 1, can then be applied to both sides. In other words, the front electrode 18 and the back electrode 14 can be configured identically. In this way, a difference signal of the effect of the gases present on both sides can be analyzed, using the front electrode 18 and the back electrode 14, which acts identically in this configuration, for example. In this case, a separation 22 can be separated the two gas spaces, that is to say a gas space surrounding the front electrode 18 and a gas space surrounding the back electrode 14.

FIG. 4 here shows a plan view of the configuration in accordance with FIG. 3, wherein the electrically insulating dielectric layer 16 and the front electrode 18, in particular, can be seen. Further leads can likewise be present, but are not shown in FIG. 4.

A measuring method with a sensor comprising a sensor element 10 described above can comprise the following steps, in particular: applying a voltage to the front electrode and the back electrode; exposing at least the front electrode to a gas to be measured; and qualitatively and/or quantitatively assigning at least one electrical characteristic of the sensor element on the basis of a measurement signal obtained via contacts of the front electrode and of the back electrode on the basis of the polarizability of the dielectric layer of the sensor element. In this case, in order to generate an improved selectivity, before or at the same time as the application of the AC voltage, a bias voltage, in particular DC voltage, can be impressed, such that a polarization of the polarizable species can be made possible. In this case, the bias voltage can counteract the expected measurement signal, such that the measurement signal that occurs later substantially corresponds to an alternating polarization by the AC voltage.

By way of example, the sensor signal can be evaluated with the aid of impedance measurements. In the latter, it is possible to map the effect of different polarization mechanisms in the form of a change in the real or imaginary part. In this case, the measurement frequency is preferably in the range of the resonant frequency of the relevant mechanism of the polarization or lower.

A detailed evaluation method of this type on the basis of a specific impedance is shown in FIG. 5. In this case, one possible operating mode could involve, for example, firstly aligning the dipoles by means of a bias voltage such that they cannot alter their alignment solely by means of the AC voltage signal applied during the measurement. Consequently, they do not contribute to the impedance response of the system in the form of a polarization current. If a gas to be detected then brings about a potential change counteracting the bias voltage at the front electrode 18 in such a way that the dipoles become mobile or a variable polarization is made possible by virtue of the potential change partly or completely cancelling the bias voltage, for instance, the additional polarization mechanism leads to a change in the measured impedance, such as, for instance, upon an evaluation of the real or imaginary part, as is shown in FIG. 5. In detail, FIG. 5 here shows a schematic illustration of measured impedance spectra of the gas sensor in the complex plane, wherein the real part Re(Z) is plotted on the x-axis and the imaginary part Im(Z) is plotted on the y-axis. If the ions or dipoles are mobile, or if a polarizability is possible, in principle, this leads to an additional polarization mechanism, which is represented by the dashed circle arc and thus generally leads to a change in the real part ($\Delta Re(Z)$, arrow 24) and imaginary part ($\Delta Im(Z)$, arrow 26) of the impedance at a specific measurement frequency, wherein the crosses 28, 30 in each case represent measured values at the frequency f. Highly selective and highly sensitive measurements can be carried out as a result.

If different gases to be detected bring about potential changes with opposite signs, a selectivity can be generated by means of a suitable choice of the bias voltage as is shown in FIG. 6. In this respect, in FIG. 6 the time is shown schematically on the x-axis, whereas on the y-axis a sensor signal or measurement signal is shown in the diagram a), possible opposite bias voltages are shown in the diagram b), wherein the dashed line is intended to indicate a zero voltage, and the partial pressure of a test gas I or II is shown in the diagram c). In this case, the gas I generates a negative potential change at the front electrode 18 and the gas II generates a positive potential change at the front electrode 18. If the ions or dipoles or in other words the polarizable regions are biased for example with a positive voltage by the application of a suitable DC voltage (see diagram b), region A), it is possible to reestablish their mobility through a gas that leads to a negative potential change at the gas electrode (gas I), which leads to a corresponding impedance change. A gas that leads to a positive potential change at the gas electrode (gas II) would not lead to a signal change in that case, since the dipoles still remain aligned. The same correspondingly applies to the case of negative bias voltages in the region B. The dashed line here indicates a state without a bias voltage, that is to say the state of a maximum polarizability or a maximum dipole mobility.

Figure 7:
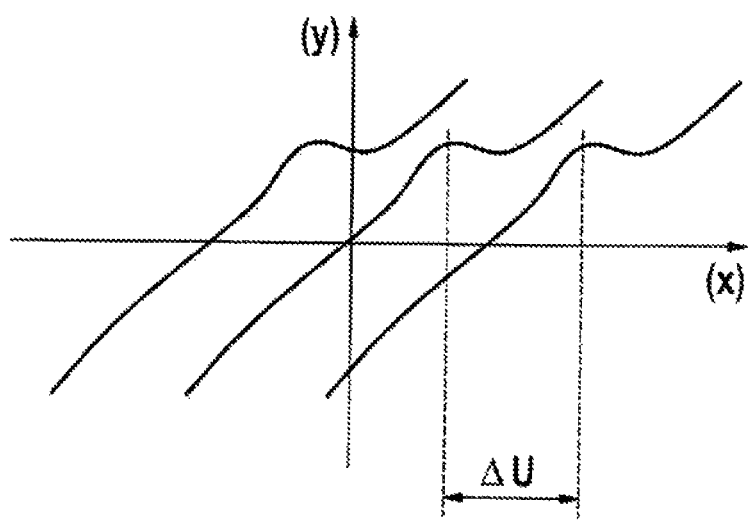
FIG. 7 shows a schematic example of an evaluation of a measurement with a sensor element by means of a current/voltage measurement.

A current-voltage measurement is possible as a further evaluation method, as is shown schematically in FIG. 7, wherein the x-axis schematically shows the voltage (U) and the y-axis schematically shows the current I. For such a measurement, firstly an, in particular negative, bias voltage is applied for some time, in order to align all the dipoles in one direction. If the voltage is then increased with a specific rate, an electronic leakage current is firstly obtained. In the region in which the direction of the electric field reverses in the dielectric, the direction of polarization of the dipoles changes and an additional, non-continuous polarization current occurs, which represents a local maximum in the I-U characteristic curve. Adsorbed gases that generate a positive/negative potential change at the gas electrode lead to a shift in the I-U curve parallel to the U-axis in a negative/positive direction. As a result, the magnitude of the shift of the curve, which can be determined with the aid of the polarization current maximum, for example, can be utilized as a sensor signal.

What is claimed is:

1. A sensor element for qualitative and/or quantitative detection of a gas, comprising:
   a front electrode configured to be exposed to a gas to be measured;
   a back electrode; and
   an electrically insulating dielectric layer positioned between the front electrode and the back electrode;
   wherein the front electrode and the back electrode are configured to be contact connected to an AC voltage source for at least one of qualitative and quantitative detection of the gas; and
   wherein the electrically insulating dielectric layer is at least locally polarizable such that, (i) when not exposed to an electric field, the electrically insulating dielectric layer is in a non-polarized state and has a first relative permittivity, and (ii) when exposed to an electric field, the electrically insulating dielectric layer is in a polarized state and at least a portion of the electrically insulating dielectric layer has a second relative permittivity, the second relative permittivity being lower than the first permittivity by a factor greater than or equal to 1.1.

2. The sensor element according to claim 1, wherein the electrically insulating dielectric layer includes at least one of mobile ions, defect associations, polar atomic groups, and polar domains, the at least one of the mobile ions, the defect associations, the polar atomic groups, and the polar domains being configured to render the electrically insulating dielectric layer at least local polarizable.

3. The sensor element according to claim 1, wherein the electrically insulating dielectric layer includes an electrically insulating material selected from the group consisting of:
   oxides including silicon dioxide, aluminum dioxide, hafnium oxide, tantalum oxide, zirconium oxide;
   nitrides including silicon nitride and boron nitride;
   carbides including silicon carbide; and
   silicides including tungsten silicide, tantalum silicide, and ferroelectric materials.

4. The sensor element according to claim 1, wherein at least one of the front electrode, the back electrode, and the electrically insulating dielectric layer has a thickness that is less than or equal to 10 µm.

5. The sensor element according to claim 1, wherein the front electrode is at least one of:
   a porous electrode; and
   an electrode formed from particles.

6. The sensor element according to claim 1, wherein the front electrode is selectively permeable to the gas.

7. The sensor element according to claim 1, wherein the back electrode is configured to be exposed to the gas.

8. A sensor arrangement, comprising:
   at least one sensor element that includes:
      a front electrode configured to be exposed to a gas to be measured;
      a back electrode; and
      an electrically insulating dielectric layer positioned between the front electrode and the back electrode;
      wherein the front electrode and the back electrode are configured to be contact connected to an AC voltage source for at least one of qualitative and quantitative detection of the gas; and
      wherein the electrically insulating dielectric layer is at least locally polarizable such that, (i) when not exposed to an electric field, the electrically insulating dielectric layer is in a non-polarized state and has a first relative permittivity, and (ii) when exposed to an electric field, the electrically insulating dielectric layer is in a polarized state and at least a portion of the electrically insulating dielectric layer has a second relative permittivity, the second relative permittivity being lower than the first permittivity by a factor greater than or equal to 1.1;
   a voltage source configured to apply a voltage to the front electrode and the back electrode, wherein the electrically insulating dielectric layer has a polarizability such that the electrically insulating dielectric layer is at least locally polarizable by the voltage; and
   an evaluation unit configured to assign at least one of a qualitative electrical characteristic and a quantitative electrical characteristic of the at least one sensor element based at least in part upon a measurement signal received via contacts of the front electrode and the back electrode, and upon the polarizability.

9. A method of at least one of qualitative and quantitative detection of a gas, comprising:
   applying a voltage to a front electrode and back electrode of a sensor element;
   wherein the sensor element further includes an electrically insulating dielectric layer positioned between the front electrode and the back electrode;
   wherein the electrically insulating dielectric layer has a polarizability such that the electrically insulating dielectric layer is at least locally polarizable by the voltage; and
   wherein, (i) when not exposed to an electric field, the electrically insulating dielectric layer is in a non-polarized state and has a first relative permittivity, and (ii) when exposed to an electric field, the electrically insulating dielectric layer is in a polarized state and at least a portion of the electrically insulating dielectric layer has a second relative permittivity, the second relative permittivity being lower than the first permittivity by a factor greater than or equal to 1.1;
   exposing at least the front electrode to a gas to be measured; and at least one of qualitatively and quantitatively assigning at least one electrical characteristic of the sensor element based at least in part upon a measurement signal received via contacts of the front electrode and back electrode, and upon the polarizability.

10. The method according to claim 9, further comprising applying a bias voltage to the front electrode and the back electrode, wherein the bias voltage is applied before or during the applying of the voltage.

* * * * *